US006911216B1

(12) United States Patent
Roth et al.

(10) Patent No.: US 6,911,216 B1
(45) Date of Patent: *Jun. 28, 2005

(54) TARGETED DELIVERY VIA BIODEGRADABLE POLYMERS

(75) Inventors: Laurence A. Roth, Windham, NH (US); Stephen Jack Herman, Andover, MA (US)

(73) Assignee: Genzyme Corporation, Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 685 days.

(21) Appl. No.: 09/195,340

(22) Filed: Nov. 18, 1998

Related U.S. Application Data

(62) Division of application No. 08/787,647, filed on Jan. 23, 1997, now Pat. No. 5,879,713, which is a continuation of application No. 08/322,092, filed on Oct. 12, 1994, now abandoned.

(51) Int. Cl.[7] .......................... A61K 9/16; A61K 38/18; A61K 38/19
(52) U.S. Cl. ....................... 424/489; 424/501; 424/423; 514/2; 514/21; 514/964; 514/965; 514/824
(58) Field of Search ................................ 424/489, 501, 424/423; 514/2, 21, 694, 695, 824

(56) References Cited

U.S. PATENT DOCUMENTS

| | | | |
|---|---|---|---|
| 3,663,588 A | | 5/1972 | Evans |
| 3,949,068 A | * | 4/1976 | Polin ........................... 424/79 |
| 4,345,588 A | | 8/1982 | Widder |
| 4,522,811 A | | 6/1985 | Eppstein et al. |
| 4,708,861 A | | 11/1987 | Popescu et al. |
| 4,745,160 A | | 5/1988 | Churchill et al. |
| 4,897,308 A | | 1/1990 | Vanlerberghe et al. |
| 4,904,479 A | | 2/1990 | Illum et al. |
| 5,057,304 A | | 10/1991 | Kretzschmar |
| 5,194,654 A | | 3/1993 | Hostetler et al. |
| 5,206,023 A | * | 4/1993 | Hunziker ..................... 424/423 |
| 5,223,263 A | | 6/1993 | Hostetler et al. |
| 5,231,580 A | | 7/1993 | Cheung et al. |
| 5,238,470 A | | 8/1993 | Tolles et al. |
| 5,264,618 A | | 11/1993 | Felgner et al. |
| 5,288,502 A | | 2/1994 | McGinity et al. |
| 5,290,552 A | * | 3/1994 | Sierra ....................... 424/94.64 |
| 5,328,471 A | | 7/1994 | Slepian |
| 5,399,346 A | | 3/1995 | Anderson et al. |
| 5,419,917 A | | 5/1995 | Chen et al. |
| 5,423,778 A | | 6/1995 | Eriksson et al. |
| 5,494,677 A | | 2/1996 | Giampapa |
| 5,512,294 A | | 4/1996 | Li et al. |
| 5,591,625 A | | 1/1997 | Gerson et al. |
| 5,607,694 A | * | 3/1997 | Marx .......................... 424/450 |
| 5,626,863 A | * | 5/1997 | Hubbell et al. .............. 424/426 |
| 5,652,225 A | | 7/1997 | Isner |
| 5,858,345 A | * | 1/1999 | Charles ..................... 424/78.04 |

FOREIGN PATENT DOCUMENTS

| | | |
|---|---|---|
| EP | 0 248 531 | 12/1987 |
| EP | 0 620 277 A1 | 10/1994 |
| WO | WO 85/03640 | 2/1985 |
| WO | WO 90/11092 | 10/1990 |
| WO | WO 92/05866 | 10/1991 |
| WO | WO 93/00051 | 6/1992 |
| WO | WO 93/14778 | 8/1993 |
| WO | WO 93/16687 | 9/1993 |
| WO | WO 93/17669 | 9/1993 |
| WO | WO 94/23699 | 10/1994 |
| WO | WO 94/24962 | 11/1994 |
| WO | WO 94/27612 | 12/1994 |
| WO | WO 94/29469 | 12/1994 |
| WO | WO 95/22316 | 2/1995 |

OTHER PUBLICATIONS

Arras, Nature Biotechnology 16:159–162 (1998).

Battler, et al., "Intracoronary Injection of Basic Fibroblast-Growth Factor and Angiogenesis in Infarcted Swine Myocardium," *J. Am. Coll. Cariol.* 22:2001–2006 (1993).

Beck, L.R., et al., "A New Long–Acting Injectable Microcapsule System for the Administration of Progesterone," *Fertil. Steril.*, 31, 545 (1979).

Benita, S., et al., "Characterization of Drug–Loaded Poly(d,l–lactide) Microspheres," *J. Pharm. Sci.*, 73, 1721 (1984).

Debs, Robert J., et al., "Transfections of animal cells in vivo with DNA in cationic liposomes for gene therapy," CA Selects: Controlled Release Technology, Abstract 120:86450c (1994).

Finkel, Toren and Stephen E. Epstein, "Gene therapy for vascular disease," *FASEB* 9:843–850 (1995).

(Continued)

*Primary Examiner*—Gollamudi S. Kishore
(74) *Attorney, Agent, or Firm*—Isabelle A.S. Blundell

(57) ABSTRACT

Delivery of bioactive molecules such as nucleic acid molecules encoding a protein can be significantly enhanced by immobilization of the bioactive molecule in a polymeric material adjacent to the cells where delivery is desired, where the bioactive molecule is encapsulated in a vehicle such as liposomes which facilitates transfer of the bioactive molecules into the targeted tissue. Targeting of the bioactive molecules can also be achieved by selection of an encapsulating medium of an appropriate size whereby the medium serves to deliver the molecules to a particular target. For example, encapsulation of nucleic acid molecules or biologically active proteins within biodegradable, biocompatible polymeric microparticles which are appropriate sized to infiltrate, but remain trapped within, the capillary beds and alveoli of the lungs can be used for targeted delivery to these regions of the body following administration to a patient by infusion or injection.

11 Claims, No Drawings

OTHER PUBLICATIONS

Flaim, et al., "Multiple Simultaneous Determinations of Hemodynamics and Flow Distribution in Conscious Rat," *J. Pharmacol. Meth.* 11:1–39 (1984).

Heymann, et al., "Blood Flow Measurements with Radionuclide–labeled Particles," *Prog. Cardiovasc. Dis.* 20:55–79 (1977).

Hill–West, J., "Prevention of Postoperative Adhesions in the Rat by In Situ Photopolymerization of Bioresorbable Hydrogel Barriers," *Obst. & Gynecol.* 83:59–64 (1994).

Hill–West et al., "Inhibition of thrombosis and intimal thickening by in situ photopolymerization of thin hydrogel barriers," *Proc. Nat. Acad. Sci.* USA 91:5967–5971 (1994).

Leclerc, Guy, et al., "Percutaneous Arterial Gene Transfer in a Rabbit Model," *J. Clin. Invest.* 90:936–944 (1992).

Losordo, Douglas, W., et al., "Use of the Rabbit Ear Artery to Serially Assess Foreign Protein Secretion After Site–Specific Arterial Gene Transfer In Vivo," *Circulation* 89:785–792 (1994).

Mathiowitz, E., et al., "Novel Microcapsules for Delivery Systems," *Reactive Polymers*, 6, 275 (1987).

Mathiowitz, E., et al., "Morphology of Polyanhydride Delivery System," *J. Scanning Microscopy*, 4, 329 (1990).

Morgan, Richard A. and W. French Anderson, "Human Gene Therapy," *Ann. Rev. Biochem.*, 62:191 (1993).

Mulligan, Richard C., "The Basic Science of Therapy," *Science* 260:926 (1993).

Nabel, Elizabeth G., et al., "Transduction of a foreign histocompatibility gene into the arterial wall induces vasculitis," *Proc. Natl. Acad. Sci.* USA 89:5157–5161 (1992).

Nabel, Elizabeth G., et al., "Site–Specific Gene Expression in Vivo by Direct Gene Transfer into the Arterial Wall," *Reports* 1285–1287 (1990).

Nikol, Sigrid, et al., "Expression of Transforming Growth Factor–$\beta$–1 Is Increased in Human Vascular Restenosis Lesions," *J. Clin. Invest.* 90:1582–1592 (1992).

Ohno, Takeshi, et al., "Gene Therapy for Vascular Smooth Muscle Cell Proliferation After Arterial Injury," *Science* 265:781–784 (1994).

Ouriemchi, E.M., et al., "Dosage Form for Controlled Delivery to the Intestine of a Drug Soluble in Gastric Liquid and Poorly Soluble in Intestinal Liquid," *J. of Polymer Eng.* 13:73–85 (1994).

O'Mullane, et al., Annals of the new York Acad Sci., 507:121–140 (1987).

Pickering, J. Geoffrey, et al., "Liposome–Mediated Gene Transfer Into Human Vascular Smooth Muscle Cells," *Circulation* 89:13–20 (1994).

Pu, Li–Qun, et al., "Angiogenic Growth Factor and Revascularization of the Ischemic Limb: Evaluation in a Rabbit Model," *J. Surg. Res.* 54:575–583 (1993).

Pu, et al., "Vascular endothelial growth factor induces dose–dependent revascularization in a rabbit model of persistent limb ischemia," *Circulation* 88(4):147 (1993) Abstract No. 0780.

Rosenfeld, Kenneth, et al., "Images in Clinical Medicine," *New England Journal of Medicine* p. 620 (Aug. 26, 1993).

Takeshita, Satoshi, et al., "Increased Gene Expression after Liposome–mediated Arterial Gene Transfer Associated with Intimal Smooth Muscle Cell Proliferation," *J. Clin. Invest.*, 93:652–661 (1994).

Takeshita, Satoshi, et al., "Therapeutic Angiogenesis," *J. Clin. Invest.*, 93:662–670 (1994).

Takeshita, Satoshi, et al., "In Vivo Evidence of Enhanced Angiogenesis Following Direct Arterial Gene Transfer of the Plasmid Encoding Vascular Endothelial Growth Factor," *Circulation* 88(4):476 (1993) Abstract No. 2565.

Tolstoshev, Paul, "Gene Therapy, Concepts, Current Trials and Future Directions," *Ann. Rev. Pharm. Toxicol.*, 32:573 (1993).

Vandorpe et al. Biomaterials 18(17):1147–1152 (1997).

Anderson, "Clinical phamacokinetic advantages of new drug delivery methods for the treatment of liver tumors," *Clinical Pharmacokinet* 27(3):191–201 (1994).

Davis, et al., "Microspheres for targeting drugs to specific body sites," *J Controlled Release* 24:157–63 (1993).

Debs, et al., "Selective enhancement of pentamidine uptake in the lung by aerosolization and delivery in liposomes," *Am Rev Respir Dis* 135(3):731–737 (1987).

Kerr, et al., *Cancer* 62:878–883 (1988).

Madoule, et al., "Chemoembolization: Principle and Perspectives," *J Microencapsul* 1(1):21–25 (1984).

Menstrup, "Validierung der Herstellung und Depoteffekt wirkostoffhaltiger Liposomen," PhD Thesis, University of Heidelberg, 1988).

Tripathi, et al., "Aminophylline targeting to lung: optimization of the size and drug loading of albumin microspheres," *J Microencapsul* 5(1):13–20 (1988).

Tumer, et al., "Fate of cholesterol–rich liposomes after subcutaneous injection into rats," *Biochim Acta* 760(1):119–25 (1983).

Wilmott, et al., *Biopharmaceutics & Drugs Disposition* 6:91–104 (1985).

Wright, et al., "Microencapsules for arterial chemoembolization: appearance and invitro drug releae characteristics," *J Microencapsul* 5(1):13–20 (1988).

* cited by examiner

TARGETED DELIVERY VIA BIODEGRADABLE POLYMERS

This application is a divisional of prior U.S. Ser. No. 08/787,647, filed on Jan. 23, 1997, by Laurence A. Roth and Stephen J. Herman for "TARGETED DELIVERY VIA BIODEGRADABLE POLYMERS", U.S. Pat. No. 5,879,713, which is a continuation of U.S. Ser. No. 08/322,092, filed Oct. 12, 1994, now abandoned.

BACKGROUND OF THE INVENTION

This invention is generally in the area of drug delivery and gene therapy devices and more specifically in the area of delivery of drugs and gene transfer via polymeric microparticles, including liposomes in a polymeric matrix.

A variety of materials have been developed for delivery of drugs, nucleic acids, and biologics. Examples include microspheres, microcapsules, and microparticles formed of biodegradable or non-biodegradable polymers which release the incorporated material over time or following exposure to specific conditions. Targeting of the materials, other than through direct administration at the targeted site, has been very difficult. Most are administered systemically if multiple release sites are required.

More recently, polymeric gels or films have been utilized for drug delivery and gene therapy, especially of small oligonucleotides such as antisense. Liposomes have also been utilized for delivery of genetic material, with varying degrees of success, primarily due to the inherent instability and short half-lives of the liposomes.

Gene therapy is typically used to refer to delivery of nucleic acid molecules which control expression of a particular endogenous gene, or to delivery and expression of an exogenous gene, which functions in addition to, or in place of, a defective or missing endogenous gene.

Three methodologies have been developed as the principal mechanisms for gene therapy: delivery via cationic lipids, for example, in the form of liposomes or vesicles, molecular conjugates, and recombinant viral vectors. These methods were recently reviewed by Morgan, *Ann. Rev. Biochem.*, 62:191 (1993), Mulligan, *Science* 260:926 (1993), and Tolstoshev, *Ann. Rev. Pharm. Toxicol.*, 32:573 (1993).

Although the three major groups of gene transduction methodology are relatively efficient, the percentage of targeted cells that can be transduced in vivo remains relatively low. To treat conditions requiring a higher percentage of gene transduction, new technologies for increasing the percentage of transduced cells would be very useful.

Furthermore, it is very difficult to target cells for delivery of genes, other than through local administration or through selection of viral vectors which infect only certain types of cells, such as replicating cells. Local delivery has advantages in that the effective local concentration is much higher than can normally be achieved by systemic administration, while the systemic concentration remains very low, thereby avoiding serious side effects. There are few methods available, however, which allow one to target scattered areas throughout the body, to achieve local release without systemic involvement.

The ability to express recombinant genes in the blood vessel wall has raised prospects for gene therapy of vascular disease. Two general approaches to introducing genes into the vessel wall have been studied. In one approach, referred to as direct gene transfer, target cells are first isolated and gene transfer is accomplished in vitro; cells that express the recombinant gene product are then selected and transplanted into the host vessel wall. In the second approach, genes are delivered "in situ" to cells within the vessel wall; this direct, in vivo approach to delivery of genes is attractive as a therapeutic modality since it mitigates the need to remove vascular cells from the patient. Since direct gene transfer precludes the opportunity to select for positive transfectants, however, it is essential that an adequate amount of DNA be introduced and expressed by the target tissue. Vascular smooth muscle cells may be suitable targets for the direct gene transfer approach because of their proximity to the lumen surface and abundance in the vessel wall.

Furthermore, abnormal accumulation of smooth muscle cells is a feature of atherosclerosis and of certain accelerated forms of vascular disease, such as restenosis following balloon angioplasty.

One potential means of transfecting smooth muscle cells within the vessel wall is through the use of cationic liposomes. Liposome-mediated gene transfer is a convenient method of transferring recombinant DNA into cells and has been used to directly transfect the arterial wall of live animals. The efficiency of successful gene transfer using cationic liposomes, however, is variable and highly dependent on the cell type. Most in vitro experience to date has been with continuous/immortal animal cells lines. The results studied using these types of cells, however, have uncertain implications for the likelihood success of direct arterial gene transfer in patients.

Local delivery of growth factors has been attempted in several ways. Takeshita, et al., *J. Clin. Invest.*, 93:662–670, (1994), delivered a bolus of a transforming vector for the growth factor VEGF to rabbits. Unfortunately, delivery was not limited to a local area. U.S. Pat. No. 5,238,470 Nabel et al discloses administering transforming vectors to arteries via a double-balloon catheter. A major limitation to this method is that the genetic material is administered all at once, resulting in inefficient transduction. A further limitation is that Nabel requires a substantial instillation time, approximately 30 minutes, resulting in prolonged arterial blockage.

There is therefore a need for an improved, specific delivery means for nucleic acid molecules and other drugs, or bioactive molecules.

It is therefore an object of the present invention to provide a method and means for targeted delivery of bioactive molecules, especially nucleic acid molecules, to tissues or cells in a patient.

It is a further object of the present invention to provide a delivery means that protects the bioactive molecules from proteases and nucleases.

It is still a further object of the present invention to provide a means for locally administering bioactive molecules to tissues or cells in a patient in a controlled, sustained manner.

SUMMARY OF THE INVENTION

Delivery of bioactive molecules such as nucleic acid molecules encoding a protein can be significantly enhanced by immobilization of the bioactive molecule in a polymeric material adjacent to the cells where delivery is desired, where the bioactive molecule is encapsulated in a vehicle such as liposomes which facilitates transfer of the bioactive molecules into the targeted tissue. Targeting of the bioactive molecules can also be achieved by selection of an encapsulating medium of an appropriate size whereby the medium serves to deliver the molecules to a particular target. For example, encapsulation of nucleic acid molecules or biologically active proteins within biodegradable, biocompatible polymeric microparticles which are appropriate sized to infiltrate, but remain trapped within, the capillary beds and alveoli of the lungs can be used for targeted delivery to these regions of the body following administration to a patient by infusion or injection.

Examples demonstrate delivery of DNA via a polymeric gel and encapsulated within liposomes which are immobilized in polymeric gel. Immobilization of the DNA in the gel increases delivery approximately 300%; immobilization of the DNA in a penetration enhancer, such as liposomes, which are then immobilized in the polymeric gel increases the delivery approximately 600 to 700%. This is measured based on luciferase expression and detection of Turner Light units.

DETAILED DESCRIPTION OF THE INVENTION

Targeted, enhanced delivery of biologically active molecules is enhanced by the use of polymeric carriers for targeting of the molecules to specific areas. In one embodiment, the polymeric carrier is a hydrogel which serves to immobilize the bioactive molecules at the site of release. In another embodiment, the polymeric carrier is in the form of microparticles that are targeted by size and degradation and release properties to particular regions of the body, especially the alveoli and capillaries.

Polymeric Carriers

Selection of Polymeric Material

Polymeric carriers must be biodegradable, sufficiently porous to permit efflux of the biologically active molecules, and sufficiently non-inflammatory and biocompatible so that inflammatory responses do not prevent the delivery of the biologically active molecules to the tissue. It is advantageous if the carrier also provides at least partial protection of the biologically active molecules from adverse effects of proteases and nucleases. In addition, it is advantageous if controlled, sustained delivery can be obtained using the polymeric carriers.

Many polymers can be utilized to form the carrier, which can be a hydrogel, organogel, film, or microparticle. Microparticles include microspheres, microcapsules, and, as used herein, liposomes, which can be further encapsulated within a polymeric matrix. The polymeric matrix serves to immobilize the microparticles at a particular site, enhancing targeted delivery of the encapsulated biologically active molecules.

Suitable polymers that can be used include soluble and insoluble, biodegradable and nonbiodegradable polymers. These can be hydrogels or thermoplastics, homopolymers, copolymers or blends, natural or synthetic.

Rapidly bioerodible polymers such as poly[lactide-co-glycolide], polyanhydrides, and polyorthoesters, whose carboxylic groups are exposed on the external surface as their smooth surface erodes, are excellent candidates for drug delivery systems. In addition, polymers containing labile bonds, such as polyanhydrides and polyesters, are well known for their hydrolytic reactivity. Their hydrolytic degradation rates can generally be altered by simple changes in the polymer backbone.

Representative natural polymers include proteins, such as zein, modified zein, casein, gelatin, gluten, serum albumin, or collagen, and polysaccharides, such as cellulose, dextrans, polyhyaluronic acid, polymers of acrylic and methacrylic esters and alginic acid. Representative synthetic polymers include polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof. Synthetically modified natural polymers include alkyl celluloses, hydroxyalkyl celluloses, cellulose ethers, cellulose esters, and nitrocelluloses. Other polymers of interest include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly (ethylene glycol), poly(ethylene oxide), poly (ethylene terephthalate), poly(vinyl acetate), polyvinyl chloride, polystyrene, polyvinyl pyrrolidone, and polyvinylphenol. Representative bioerodible polymers include polylactides, polyglycolides and copolymers thereof, poly(ethylene terephthalate), poly(butic acid), poly(valeric acid), poly (lactide-co-caprolactone), poly[lactide-co-glycolide], polyanhydrides, polyorthoesters, blends and copolymers thereof.

These polymers can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif. or else synthesized from monomers obtained from these suppliers using standard techniques.

Suitable polymer compositions preferably have intrinsic and controllable biodegradability, so that they persist for about a week to about six months; are non-toxic, containing no significant toxic monomers and degrading into non-toxic components; are biocompatible; are chemically compatible with the substances to be delivered, and tend not to denature the active substance; are sufficiently porous to allow the incorporation of biologically active molecules and their subsequent liberation from the polymer by diffusion, erosion or a combination thereof; are able to remain at the site of application by adherence or by geometric factors, such as by being formed in place or softened and subsequently molded or formed into microparticles which are trapped at a desired location; are capable of being delivered by techniques of minimum invasivity, such as by catheter, laparoscope or endoscope. Types of monomers, macromers, and polymers that can be used are described in more detail below.

Hydrogels

Hydrogels are preferred embodiments for application to a tissue for direct delivery since they intrinsically have most of these desirable properties. Particularly preferred are gels which are composed predominantly of polyethylene glycol. These can be applied by direct photopolymerization with an initiator, by chemical polymerization with a peroxygen, or by "interfacial" photopolymerization, with a dye adsorbed to the tissue to be coated, as described below.

Examples of these macromers are PEG-oligolactyl-acrylates, as described by Hill-West, et al., Proc. Natl. Acad.

Sci. USA 91:5967–5971, 1994; Obst. & Gynecol. 83:59–64, 1994. The choice of appropriate end caps permits rapid photopolymerization and gelation; acrylates can be polymerized using several initiating systems, e.g., an eosin dye, by brief exposure to ultraviolet or visible light. Poly (ethyleneglycol) or a PEG central structural unit (core) is useful on the basis of its high hydrophilicity and water solubility, accompanied by excellent biocompatibility. A short poly($\alpha$-hydroxy acid), such as polyglycolic acid, is a preferred chain extension because it rapidly degrades by hydrolysis of the ester linkage into glycolic acid, a harmless metabolite. Although highly crystalline polyglycolic acid is insoluble in water and most common organic solvents, the entire macromer is water-soluble and can be rapidly gelled into a biodegradable network while in contact with aqueous tissue fluids. Such networks can be used to entrap and homogeneously disperse water-soluble drugs and enzymes and to deliver them at a controlled rate. Other preferred chain extensions are polylactic acid, polycaprolactone, polyorthoesters, and polyanhydrides. Polypeptides may also be used.

These materials are particularly useful for controlled delivery, especially of hydrophilic materials, since the water soluble regions of the polymer enable access of water to the materials entrapped within the polymer. Moreover, it is possible to polymerize the macromer containing the material to be entrapped without exposing the material to organic solvents. Release may occur by diffusion of the material from the polymer prior to degradation and/or by diffusion of the material from the polymer as it degrades, depending upon the characteristic pore sizes within the polymer, which is controlled by the molecular weight between crosslinks and the crosslink density. Deactivation of the entrapped material is reduced due to the immobilizing and protective effect of the gel and catastrophic burst effects associated with other controlled-release systems are avoided. When the entrapped material is an enzyme, the enzyme can be exposed to substrate while the enzyme is entrapped, provided the gel proportions are chosen to allow the substrate to permeate the gel. Degradation of the polymer facilitates eventual controlled release of free macromolecules in vivo by gradual hydrolysis of the terminal ester linkages.

An advantage of these macromers are that they can be polymerized rapidly in an aqueous surrounding. Precisely conforming, semi-permeable, biodegradable films or membranes can thus be formed on tissue in situ to serve as biodegradable barriers, as carriers for living cells or other biologically active materials, and as surgical adhesives. In a particularly preferred embodiment, the macromers are applied to tissue having a photoinitiator bound thereto, and polymerized to form an ultrathin coating. This is especially useful in forming coatings on the inside of tissue lumens such as blood vessels where there is a concern regarding restenosis, and in forming tissue barriers during surgery which thereby prevent adhesions from forming.

In general terms, the macromers are polymers that are soluble in aqueous solutions, or nearly aqueous solutions, such as water with added dimethylsulfoxide. They have three components including a biodegradable region, preferably hydrolyzable under in vivo conditions, a water soluble region, and at least two photopolymerizable regions. The term "at least substantially water soluble" is indicative that the solubility should be at least about 5 g/100 ml of aqueous solution. The term "polymerizable" means that the regions have the capacity to form additional covalent bonds resulting in macromer interlinking, for example, carbon-carbon double bonds of acrylate-type molecules. Such polymerization is characteristically initiated by free-radical formation resulting from photon absorption of certain dyes and chemical compounds to ultimately produce free-radicals.

In a preferred embodiment, a hydrogel is formed from a biodegradable, polymerizable, macromer including a core, an extension on each end of the core, and an end cap on each extension. The core is a hydrophilic polymer or oligomer; each extension is a biodegradable oligomer; and each end cap is an oligomer, dimer or monomer capable of cross-linking the macromers. In a particularly preferred embodiment, the core includes hydrophilic poly(ethylene glycol) oligomers of molecular weight between about 400 and 30,000 Da; each extension includes biodegradable poly ($\alpha$-hydroxy acid) oligomers of molecular weight between about 200 and 1200 Da; and each end cap includes an acrylate-type monomer or oligomer (i.e., containing carbon-carbon double bonds) of molecular weight between about 50 and 200 Da which are capable of cross-linking and polymerization between copolymers. More specifically, a preferred embodiment incorporates a core consisting of poly (ethylene glycol) oligomers of molecular weight about 10,000 Da; extensions consisting of poly(glycolic acid) oligomers of molecular weight about 250 Da; and end caps consisting acrylate moieties of about 100 Da molecular weight.

Examples of suitable materials for use as the core water soluble region are poly(ethylene glycol), poly(ethylene oxide), poly(vinyl alcohol), poly(vinylpyrrolidone), poly (ethyloxazoline), poly(ethylene oxide)-co-poly (propyleneoxide) block copolymers, polysaccharides or carbohydrates such as hyaluronic acid, dextran, heparin sulfate, chondroitin sulfate, heparin, or alginate, or proteins such as gelatin, collaqen, albumin, or ovalbumin.

Biodegradable regions can be constructed from polymers or monomers using linkages susceptible to biodegradation, such as ester, peptide, anhydride, orthoester, and phosphoester bonds.

Examples of biodegradable components which are hydrolyzable are polymers and oligomers of glycolide, lactide, $\epsilon$-caprolactone, other $\alpha$-hydroxy acids, and other biologically degradable polymers that yield materials that are non-toxic or present as normal metabolites in the body. Preferred poly($\alpha$-hydroxy acid)s are poly(glycolic acid), poly(DL-lactic acid) and poly(L-lactic acid). Other useful materials include poly(amino acids), poly(anhydrides), poly (orthoesters), and poly(phosphoesters). Polylactones such as poly($\epsilon$-caprolactone), poly($\epsilon$(3 caprolactone), poly($\delta$-valerolactone) and poly(gamma-butyrolactone), for example, are also useful.

The polymerizable regions are preferably polymerized using free radicals generated by a photoinitiator. The photoinitiator preferably uses the visible or long wavelength ultraviolet radiation. Preferred polymerizable regions are acrylates, diacrylates, oligoacrylates, dimethacrylates, oligomethoacrylates, or other biologically acceptable photopolymerizable groups. A preferred tertiary amine is triethanol amine.

Useful photoinitiators are those which initiate free radical polymerization of the macromers without cytotoxicity and within a short time frame, minutes at most and preferably seconds. Preferred initiators for initiation using long wavelength ultraviolet photoradiation are ethyl eosin, 2,2-dimethoxy-2-phenyl acetophenone, other acetophenone derivatives, and camphorquinone. In all cases, crosslinking and polymerization are initiated among copolymers by a light-activated free-radical polymerization initiator such as 2,2-dimethoxy-2-phenylacetophenone or a combination of ethyl eosin ($10^{-4}$–$10^{-2}$ mM) and triethanol amine (0.001 to 0.1 M), for example.

In another embodiment, the process is carried out by providing a material that is conformable, at least temporarily, at body temperature, yet which may be rendered non-conformable upon completion of the deposition process, such as a poloxamer™ (a polyethylene oxide-polyethylene glycol block copolymer). Poloxamer™ can be selected which are liquid at room temperature and solid at body temperature.

Pavings or Films

In other embodiments, such as that described in U.S. Pat. No. 5,231,580 to Slepian, polymeric pavings or films are applied to the tissue using a catheter, endoscope or laparoscope. Preferred polymers include polyhydroxy acids such as polylactic acid, polyglycolic acid and copolymers thereof, polycaprolactone, polyanhydrides, polyorthoesters, and other materials commonly used for implantation or sutures.

The basic requirements for the material to be used in the process are biocompatibility and the capacity to be chemically or physically reconfigured under conditions which can be achieved in vivo. Such reconfiguration conditions preferably involve photopolymerization, but can involve heating, cooling, mechanical deformation, (such as stretching), or chemical reactions such as polymerization or crosslinking.

In their conformable state, the coating materials may exhibit a wide variety of forms. They can be present as polymers, monomers, macromers or combinations thereof, maintained as solutions, suspensions, or dispersions.

Microparticles

In a preferred embodiment, the microparticle has a diameter which is selected to lodge in particular regions of the body. Use of microspheres that lodge within organs or regions is known in studies of blood flow (Flaim et al, J Pharmacol. Meth. 11:1–39, 1984; Heymann et al, Prog. Cardiovasc. Dis. 20:55–79, 1977), but not in delivery of active materials. For example, a microparticle selected to lodge in a capillary will typically have a diameter of between 10 to 25, most preferably 15 to 20 microns. Numerous methods are known for preparing microparticles of any particular size range. In the various applications of the present invention, the sizes may range from 0.2 micron up to 100 microns. Synthetic methods for gel microparticles, or for microparticles from molten materials, are known, and include polymerization in emulsion, in sprayed drops, and in separated phases. For solid materials or preformed gels, known methods include wet or dry milling or grinding, pulverization, classification by air jet or sieve, and the like.

Microparticles can be fabricated from different polymers using a variety of different methods known to those skilled in the art. Exemplary methods include those set forth below.

Polylactic acid blank microparticles were fabricated using three methods: solvent evaporation, as described by E. Mathiowitz, et al., *J. Scanning Microscopy,* 4, 329 (1990); L. R. Beck, et al., *Fertil. Steril.,* 31, 545 (1979); and S. Benita, et al., *J. Pharm. Sci.,* 73, 1721 (1984); hot-melt microencapsulation, as described by E. Mathiowitz, et al., *Reactive Polymers,* 6, 275 (1987); and spray drying. Polyanhydrides made of bis-carboxyphenoxypropane and sebacic acid with molar ratio of 20:80 P(CPP-SA) (20:80) (Mw 20,000) were prepared by hot-melt microencapsulation.

Poly(fumaric-co-sebacic) (20:80) (Mw 15,000) blank microparticles were prepared by hot-melt microencapsulation. Polystyrene microparticles were prepared by solvent evaporation.

Hydrogel microparticles were prepared by dripping a polymer solution from a reservoir though microdroplet forming device into a stirred ionic bath. The specific conditions for alginate, chitosan, alginate/polyethylenimide (PEI) and carboxymethyl cellulose (CMC) are listed in Table 1.

a. Solvent Evaporation. In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid microparticles. Several different polymer concentrations were used: 0.05–0.20 g/ml. The solution is loaded with a drug and suspended in 200 ml of vigorously stirred distilled water containing 1% (w/v) poly (vinyl alcohol) (Sigma). After 4 hours of stirring, the organic solvent evaporates from the polymer, and the resulting microparticles are washed with water and dried overnight in a lyophilizer. Microparticles with different sizes (1–1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

b. Hot Melt Microencapsulation. In this method, the polymer is first melted and then mixed with the solid particles of dye or drug that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microparticles are washed by decantation with petroleum ether to give a free-flowing powder. Microparticles with sizes between one to 1000 microns are obtained with this method. The external surfaces of spheres prepared with this technique are usually smooth and dense. This procedure is used to prepare microparticles made of polyesters and polyanhydrides. However, this method is limited to polymers with molecular weights between 1000–50,000.

c. Solvent Removal. This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. Microparticles that range between 1–300 microns can be obtained by this procedure. The external morphology of spheres produced with this technique is highly dependent on the type of polymer used.

d. Spray-Drying In this method, the polymer is dissolved in methylene chloride (0.04 g/mL). A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24° C., outlet temperature=13–15° C., aspirator setting=15, pump setting= 10 mL/minute, spray flow=600 Nl/hr, and nozzle diameter= 0.5 mm. Microparticles ranging between 1–10 microns are obtained with a morphology which depends on the type of polymer used. This method is primarily used for preparing microparticles designed to improve imaging of the intestinal tract, since for this application, particle size should not exceed 10 $\mu$.

e. Hydrogel Microparticles

Microparticles made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100–170 RPM) ionic hardening bath is positioned below the extruding device to catch the forming microdroplets. The microparticles are left to incubate in the bath for twenty to thirty minutes in order to allow sufficient time for gelation to occur. Microparticle particle size is controlled by using various size extruders or varying either the nitrogen gas or polymer solution flow rates.

The matrix is preferably in the form of a microparticle such as a microsphere (where the biologically active molecules are dispersed throughout a solid polymeric matrix) or microcapsule (where the biologically active molecules are encapsulated in the core of a polymeric shell). The size and composition of the polymeric device is selected to result in favorable release kinetics in tissue. The size is also selected according to the method of delivery which is to be used, typically injection into a tissue or administration of a suspension by aerosol into the nasal and/or pulmonary areas, and where appropriate, entrapment at the site where release is desired. The matrix composition can be selected to not only have favorable degradation rates, but to be formed of a material which is bioadhesive, to further increase the effectiveness of transfer when administered to a mucosal surface, or selected not to degrade initially but to release by diffusion over an extended period.

Liposomes are available commercially from a variety of suppliers. Alternatively, liposomes can be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

Biologically Active Molecules

Biologically active molecules which can be incorporated into the polymeric carrier, directly and/or indirectly, i.e., within microparticles which are immobilized in the carrier, include proteins, nucleic acid molecules, carbohydrates, lipids, and combinations thereof. Examples of proteins include cytokines such as interferons and interleukins, poetins, and colony-stimulating factors, growth factors, angiogenic factors and fragments thereof. Examples of nucleic acid molecules include genes and cDNAs encoding proteins, expression vectors, antisense and other oligonucleotides such as ribozymes which can be used to regulate or prevent gene expression. Carbohydrates include Sialyl Lewis$^x$ which has been shown to bind to receptors for selectins to inhibit inflammation. Growth factors in the broad sense are preferred biologically active molecules. A "deliverable growth factor equivalent" (abbreviated DGFE) is a growth factor for a cell or tissue, broadly construed, including growth factors, cytokines, interferons, interleukins, proteins, colony-stimulating factors, gibberellins, auxins, and vitamins; further including peptide fragments or other active fragments of the above; and further including vectors, i.e., nucleic acid constructs capable of synthesizing such factors in the target cells, whether by transformation or transient expression; and further including effectors which stimulate or depress the synthesis of such factors in the tissue, including natural signal molecules, antisense and triplex nucleic acids, and the like. Particularly preferred DGFE's are vascular endothelial growth factor (VEGF), endothelial cell growth factor (ECGF), basic fibroblast growth factor (bFGF), bone morphogenetic protein (BMP), and platelet derived growth factor (PDGF), and DNA's encoding for them. Preferred clot dissolving agents are tissue plasminogen activator, streptokinase, urokinase and heparin.

Incorporation of Biologically Active Molecules into the Polymeric Carriers

Generally, the biologically active molecules are mixed with the polymer at the time the material is either polymerized or when the polymer is formed into a microparticle or liposome, in a concentration which will release an effective amount at the targeted site in a patient. For example, in the case of a hydrogel, the macromer, photoinitiator, and biologically active molecules to be encapsulated are mixed in an aqueous mixture. Particles of the mixture are formed using standard techniques, for example, by mixing in oil to form an emulsion, forming droplets in oil using a nozzle, or forming droplets in air using a nozzle. The suspension or droplets are irradiated with a light suitable for photopolymerization of the macromer.

The biologically active molecules to be delivered can be mixed with the polymeric material in any of a variety of ratios, depending on the dosage of active molecule desired. The polymer in the gel will typically be at a volume concentration of 5 to 25% (wt/volume), or 50 to 250 mg/ml. Biological actives will be present at concentrations at or below 1 to 10 microgram/ml for DNA and the like, and may range up to 10 to 50 mg/ml for active proteins and the like. The exact concentration will depend on the particular active molecule, and on the effect to be achieved.

Characterization studies can be performed at different loadings to investigate encapsulation properties and morphological characteristics of the microparticles. Particle size can be measured by quasi-elastic light scattering (QELS). Drug loading can be measured by dissolving lyophilized microparticles into an appropriate solvent and assaying the amount of biologically active molecules spectrophotometrically or by other appropriate means.

Administration of the Polymeric Carrier

The polymeric carrier can be administered directly, for example, by spraying or application of a solution, or indirectly, through a catheter, endoscope, or laparoscope.

When delivered to the interior of a hollow organ, the process of application must not cause collateral injury by prolonged blockage of flow through the organ.

Preferred delivery methods are those which are minimally invasive or disruptive to the subject. These include administration of microparticles as well as percutaneous application to the interior of hollow organs or natural body cavities of a polymeric coating, film, gel, or stent. Suitable delivery devices for providing a polymer coating or layer on the surface of tissues are catheters, laparoscopes, and endoscopes, as defined in PCT/US94/04824 by Pathak et al.

Application of a Hydrogel

Photopolymerization of a hydrogel using the macromers described above can be carried out in as little as 10 seconds, using a portable, low powered long wave UV (LWUV) emitting source. Visible laser light is also useful for polymerization. Low intensity and short exposure times make visible laser light virtually harmless to living cells since the radiation is not strongly absorbed in the absence of the proper chromophore. Laser light can also be transported using fiber optics and can be focused to a very small area. For example, 0.2 ml of a 30% w/v photosensitive oligomer solution is mixed with ethyl eosin ($10^{-4}$ M) and triethanol amine (0.01 to 0.1 M) and the solution is irradiated with an argon ion laser (American argon ion laser model 905 emitting at 514 nm) at a power of 0.2–0.5 W/cm$^2$. The beam is expanded to a diameter of 3 mm and the sample is slowly scanned until gelation occurs.

In a particularly preferred application of these materials, an ultrathin coating is applied to the surface of a tissue, most preferably the lumen of a tissue such as a blood vessel. The photoinitiator is applied to the surface of the tissue, allowed to react and bond to tissue, the unbound photoinitiator is removed by dilution or rinsing, and the macromer solution is applied and polymerized. This method is capable of creating uniform polymeric coating of between 10 and 500 microns in thickness, more typically 50 to 200 microns, which does not evoke thrombosis or localized inflammation.

Application of a Paving or Coating

Local administration of a polymeric material can be performed by loading the composition in a balloon catheter, and then applying the composition directly to the inside of a tissue lumen within a zone occluded by the catheter balloons. The tissue surface may be an internal or external surface, and can include the interior of a tissue lumen or hollow space whether naturally occurring or occurring as a result of surgery, percutaneous techniques, trauma or disease. The polymeric material can then be reconfigured to form a coating or "paving" layer in intimate and conforming contact with the surface. The resulting paving layer optionally can have a sealing function. As used herein, the term "sealing" or "seal" means a coating of sufficiently low porosity that the coating provides a barrier function. The term "paving" refers to coatings in general wherein the coatings are porous or perforated or are of a low porosity "sealing" variety. The coating preferably has a thickness on the tissue surface on the order of 0.001–1.0 mm, however, coatings having a thickness outside that range may be used as well. By appropriate selection of the material employed and of the configuration of the paving material, the process can be tailored to satisfy a wide variety of biological or clinical situations.

The monomers, macromers and polymers that can be used for this application are selected from the same group as described above for formation of microparticles. Preferably, the polymeric material has a variable degree of conformability in response to a stimulus. The material is preferably substantially non-conformable in vivo upon completion of the coating process. The material, in its conformable form, can be positioned in contact with a tissue or cellular surface to be coated and then stimulated to render it non-conformable. The material is preferably rendered non-conformable by applying photochemical stimulus, but can optionally be achieved solely by chemical or thermal stimulus. The material is positioned at either an internal or external treatment location and contacted with the tissue or cellular surface to be paved or sealed, and the material is then converted into a non-conformable state to form a biocompatible coating on the tissue surface.

The coating can be applied using a catheter, such as a modified PTCA catheter. The material is preferably applied using a single catheter with single or multiple balloons and lumens. The catheter should be of relatively low cross-sectional area. A long thin tubular catheter manipulated using fluoroscopic guidance is preferred for providing access to the interior of organ or vascular areas. The material can also be applied to the surface to be coated by spraying, extruding or otherwise internally delivering the material in a conformable form via a long flexible tubular device having single or multiple lumens.

During the step of positioning the material at the desired location, the location may be accessed by either invasive surgical techniques or by relatively non-invasive techniques such as laparoscopic procedures or percutaneous transluminal procedures. The process of fixing the shape of the material can be accomplished in several ways, depending on the character of the original material. For example, in its conformable state the material can be formed using the balloon portion of a balloon catheter after which the conditions are adjusted such that the material is rendered non-conformable. In the preferred embodiment, gels are rendered non-conformable at the treatment site by photopolymerization using infrared, visible, UV, or ultrasonic radiation to the material. Optionally, the polymers can be rendered non-conformable by localized heating or by chemical means. Thermal control can be provided, for example, using a fluid flow through or into the balloon, or using a partially perforated balloon such that temperature control fluid passes through the balloon into the lumen. Thermal control can also be provided using electrical resistance heating via a wire running along the length of the catheter body in contact with resistive heating elements. This type of heating element can make use of DC or radio frequency (RF) current or external RF or microwave radiation. Other methods of achieving temperature control can also be used, including light-induced heating using an internal optical fiber (naked or lensed).

In one embodiment, the step in which the conformable material is contacted with the tissue surface may be considered as a "molding" procedure in which the conformable material is molded into substantially conforming contact with the body tissue before rendering it non-conformable. It is noted that the transition of the material from a conformable to a non-conformable state may involve a phase change in the material, however, such a phase change is not necessary. For example, in certain embodiments, the terms "conformable" and "non-conformable" are primarily relative descriptions of a material which undergoes a significant change in viscosity and flowability without undergoing an actual phase change. Alternatively, the transition of the material between its conformable and non-conformable states may be the result of an actual phase change in the material resulting either from the addition or removal of energy from the material.

The polymeric materials may be applied in custom designs, with varying thicknesses, lengths, and three-dimensional geometries (e.g. spot, stellate, linear, cylindrical, arcuate, spiral) to achieve varying finished geometries. Further, the process may be used to apply material to the inner surfaces of hollow, cavernous, or tubular biological structures (whether natural or artificially formed) in either single or multi-layer configurations. The process may also be used, when appropriate, to occlude a tissue lumen completely.

The paving coating may be applied as a continuous layer either with or without perforations. In the case in which the paving coating is applied without perforations, it is referred to as a "seal" to act as a barrier layer on the surface of the tissue. The coating can also be applied to cellular surfaces, for example, to coat or encapsulate individual or multiple cells.

Administration of Microparticles

The injectable microparticles can be administered to a patient intravenously, intramuscularly, or subcutaneously or in other known ways appropriate to the therapeutic effect desired, including as an aerosol or spray for lungs or by direct lavage through orifices. The particles can be lyophilized and then formulated into an aqueous suspension in a range of microgram/ml to 100 mg/ml prior to use.

The desired concentration of biologically active molecules in the polymeric carrier will depend on absorption, inactivation, and excretion rates of the drug as well as the delivery rate of the molecules from the carrier. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions.

The microparticles can be administered once, or may be divided into a number of smaller doses to be administered at varying intervals of time, depending on the release rate of the particle, and the desired dosage.

Solutions or suspensions used for intravenous, intramuscular, or topical application, or other delivery route can include any of the following components, as required: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, preferred carriers are physiological saline or phosphate buffered saline (PBS).

Catheters can be made of any known material, including metals, such as steel, and thermoplastic polymers. Occluding balloons can be made from compliant materials such as latex or silicone, or non-compliant materials such as polyethylene terephthalate (PET). The expansible member is preferably made from non-compliant materials such as PET, (PVC), polyethylene or nylon. If used, the balloon catheter portion of a dilatation may optionally be coated with materials such as silicones, polytetrafluoroethylene (PTFE), hydrophilic materials like hydrated hydrogels and other lubricous materials to aid in separation of the polymer coating.

In addition to blood vessels, the process may be utilized for other applications such as coating the interior of veins, ureters, urethras, bronchi, biliary and pancreatic duct systems, the gut, nasolacrimal ducts, sinus cavities, the eye, and eustachian, spermatic and fallopian tubes. Likewise the process can be used to provide a paving layer in the context of transhepatic portosystemic shunting, dialysis grafts, arterio-venous fistulae, and aortic and other arterial aneurysms. The paving and sealing material of the process can also be used in other direct clinical applications even at the coronary level. These include but are not limited to the treatment of abrupt vessel reclosure post PCTA, the "patching" of significant vessel dissection, the sealing of vessel wall "flaps" either secondary to catheter injury or spontaneously occurring, or the sealing of aneurysmal coronary dilations associated with various arteritidies. Further, the method provides intraoperative uses such as sealing of vessel anastomoses during coronary artery bypass grafting and the ability to provide a "bandaged" smooth polymer surface.

Treatment of Specific Disorders

Vascularization

A common problem in aging is atherosclerosis affecting the arteries of the lower limbs. This can cause claudication, or sharp pain when walking. This disease can be treated by inducing the creation of additional collateral circulation in the affected region (in this case, the leg) by introducing a growth factor such as VEGF (vascular endothelial growth factor), or a DNA which can express it. The growth factor or DNA can be delivered either by creating a thin coating containing the factor inside an artery leading to the region, or by injecting microparticles containing the factor into the artery feeding the affected limb or region. In the latter case, the microparticles are preferably at least 15 microns in diameter, preferably 20 microns or more, to cause the delivery particles to localize predominantly in the region. (It should be noted that some microparticles will probably exit the treated region, and lodge in the lungs or elsewhere; this effect must be accounted for in treatment planning.)

Another application includes revascularization in cardiac tissue including the myocardium, and revascularization after stroke or ischemia.

Regeneration or Repair of Tissues

Yet another application is in regeneration or repair of particular organs. Delivery of various bone morphogenetic proteins can be useful for controlled remodeling of bone, or de novo bone or cartilage formation, in which it is critical that the developmental or morphogenetic effects be strictly confined to the target site, and not exhibited throughout the organism. Local deposition of biologically active molecules can be useful in repairing bone in areas such as the nasal passages and sinuses, where precise control of positioning is required.

Examples of other tissues which can be treated in this manner include the stomach and intestines, where growth factors help accelerate repair of ulceration, repair of external ulceration of skin, and general wound repair.

Other organ systems susceptible to treatment include any organ system in which material flows through the organ from a source, so that a factor can be administered, either in a coating or as particles, for instillation into the organ to be treated by flow. Exemplary organs include lymph nodes, the bile duct, the urinary tract, the lungs, the space occupied by the cerebro-spinal fluid, and the like.

The present invention will be further understood by reference to the following non-limiting examples.

EXAMPLE 1

Gene Delivery from a Gel In Vitro

Previous work on gene transfer into arteries has involved administration of DNA in a liquid vehicle, including pressing the liquid into artery walls with a balloon catheter. For more efficient local delivery, a thin, locally-deposited gel, from which DNA can diffuse into the target tissue, was utilized.

Transfection Procedure

Positively-charged liposomes (Transfection-reagent, Boehringer Mannheim) containing the cationic lipid analogue 1,2-dioleoyloxy-3-(trimethylammonium) propane (DOTAP)* were used fOR transfections. Plasmid DNA was purified by centrifugation through a cesium chloride gradient. Five $\mu$g of DNA was mixed with 30 $\mu$g of liposomes in 200 $\mu$L of Hanks Balanced Salt Solution (HBSS, Gibco). Expression Vectors and Analysis of Recombinant Gene Expression.

*Alternative nomenclature: N-[1-(2,3-Dioleoyloxy)propyl]-N,N,N,trimethylammonium methylsulfate.

The luciferase expression vector employed was pRSV-LUC (gift of Dr. A. Brasier, Galveston, Tex., to Dr. Jeffrey M. Isner, St. Elizabeth's Hospital, Boston, Mass., who provided the vector). This contains a 5' deletion of firefly luciferase cDNA, with transcription under the control of the Rous sarcoma virus long terminal repeat promoter. Use of this reporter gene allows for quantification of gene expression in cell lysates. Cells were washed 3 times with calcium-free HBSS and extracts prepared using a cell lysis reagent (Promega, Madison Wis.) containing 1% Triton-X100™. Half of the extract was taken for analysis of total protein content, performed using the Biorad Microassay procedure. Bovine serum albumen (1 mg/ml) was added to the other half as a carrier protein and luciferase activity was measured. For this, a 20 $\mu$l aliquot was mixed at room temperature with 100 $\mu$l of luciferase assay reagent (Promega) containing beetle luciferin. Emission of light, integrated over 10 seconds, was measured using a luminometer (Turner Designs, Model 20e, Sunnyvale Calif.). Results, read as light units, were within the linear range of the detection system as evaluated using serial dilutions of a known amount of luciferase (Sigma, Product No. L-9009). Background activity, measured using phosphate-buffered saline or lysates of nontransfected cells, was consistently zero.

The plasmid pRSVLUC, obtained from the laboratory of Dr. Jeffrey Isner of St. Elizabeth's hospital in Boston, which encodes the enzyme luciferase under the control of a SV40 promoter, was dissolved in a gelling prepolymer. The prepolymer had a core of polyethylene glycol, MW8000, with about 5 lactate residues at each end, capped by an acrylate group at each end, synthesised according to the teachings of PCT US 93/17669 by Hubbell et al., hereby incorporated by reference. The polymer concentration was 10%. The application method was otherwise essentially identical to that described in Hill-West et al, Proc. Nat. Acad. Sci. USA 91:5967–5971, 1994. Tissue surfaces were stained by application of 1 mM Eosin Y, and washed. The polymer solution containing the DNA, and also 100 mM ethanolamine and 0.15% n-vinyl pyrrolidone, and was polymerized essentially as in Hill-West. The amount of plasmid in the delivery vehicle was between 0.02 and 2 micrograms. Liposomes as described above were optionally included. The luminal surface of rabbit arterial strips, which were maintained in tissue culture essentially as described by Takeshita et al., *J. Clin. Invest.*, 93:652–661, (1994), were stained with a photoinitiating dye, Eosin Y, according to PCT US 93/01776 by Hubbell et al., and washed in medium. Prepolymer solution (23% wt prepolymer solution in saline) containing DNA, with or without added liposomes (at a ratio of 4 parts by weight of liposomes per part of DNA), was applied as a spot to stained arterial strips. The solution was photopolymerized with green light to form a hydrogel. As controls, artery strips were treated with DNA/prepolymer solution, which was not gelled by photoillumination. After 7 days in culture, luciferase expression was measured in Turner Light Units per gram of tissue (TLU/g), by standard methods.

At the optimal level of DNA application (2 micrograms/dose) controls had 3.3±3.3 TLU/g; tissue treated with gels containing DNA not encapsulated within liposomes had 10.7±3.6 TLU/g; and tissue treated with gels containing DNA encapsulated within liposomes had 20.8±1.7 TLU/g.

The results demonstrate that gene transfer and expression can be accomplished by delivery with a gel, with or without liposomes, and that the efficiency of delivery is significantly higher than when the DNA is merely applied to the tissue surface. However, the results also indicate that the efficacy of transfer can be greatly increased by incorporation of the DNA into liposomes prior to immobilization.

EXAMPLE 2

In Vivo Luciferase Gene Delivery Via Photopolymerizable Hydrogel

In vivo gene delivery was demonstrated using the rat carotid artery model. Interfacially polymerized gels, prepared as described in example 1, were formed in the right carotid artery of rats. The left side was untreated and served as control. Gels contained 25 micrograms DNA per ml of prepolymer solution containing 10% w/v prepolymer encapsulated in 100 micrograms liposomes/ml of prepolymer, and otherwise were deposited as described by Hill-West et al. Arteries were illuminated with green light to polymerize the macromer, resulting in a layer about 100 micrometers thick. After 3 days, rats were sacrificed and tissue examined for luciferase expression.

No gene expression was evident in control (untreated) arteries, while treated arteries had 8.2±6.2 TLU/g.

As additional controls, DNA/macromer solutions were applied either to the adventitial (outside) surface of arteries, and flushed with saline; or were applied to the interior surface, and not illuminated. The former treatment gave 0.85±0.21 TLU/g, and the latter gave 3.9.±3.7 TLU/g.

Variations and modifications of the claimed invention will be obvious to those skilled in the art from the foregoing detailed description of the invention. It is intended that all of these variations and modifications be included within the scope of the appended claims.

We claim:

1. A method for locally delivering a biologically active molecule to a site in the vascular system where treatment is needed to promote vascularization or revascularization of a tissue, the method comprising:

a) selecting a biodegradable covalently polymerizable material, b) mixing a biologically active molecule with the material, wherein the biologically active molecule is effective to promote vascularization or revascularization of the tissue, c) applying the material to the site where treatment is needed, and d) covalently polymerizing the material to permit controlled release of a therapeutically effective amount of the biologically active molecule.

2. The method of claim 1 wherein the polymerized material is a hydrogel or an organogel.

3. The method of claim 1, wherein the biologically active molecule is selected from the group consisting of growth factors, cytokines, angiogenesis factors, peptide fragments thereof, and nucleic acid constructs capable of synthesizing these compounds.

4. The method of claim 1 in which the biologically active molecule of step (b) is entrapped in a polymer which is in the form of microparticles.

5. The method of claim 1 in which the biologically active molecule is entrapped in a material limiting its diffusion rate before being mixed into the polymerizable material.

6. The method of claim 1 wherein the biologically active molecule is selected from the group consisting of growth hormones, interferons, interleukins, and colony-stimulating factors.

7. The method of claim 1 wherein the biologically active molecule is a growth factor selected from the group consisting of vascular endothelial growth factor (VEGF), endothelial cell growth factor (ECGF), basic fibroblast growth factor (bFGF), bone morphogenic protein (BMP), platelet derived growth factor (PDGF), peptides thereof, and nucleic acid constructs capable of expressing these proteins.

8. The method of claim 1 wherein the biologically active molecule is at least one of tissue plasminogen activator, streptokinase, urokinase, and heparin.

9. The method of claim 2, wherein the material which polymerizes to form a gel is covalently polymerizable.

10. The method of claim 1, wherein the material contains a growth factor.

11. The method of claim 10 wherein the growth factor is VEGF.

* * * * *